US012150606B2

(12) United States Patent
Ciavarella et al.

(10) Patent No.: US 12,150,606 B2
(45) Date of Patent: Nov. 26, 2024

(54) TOUCH-FREE TABLETOP DISPENSERS

(71) Applicant: GOJO Industries, Inc., Akron, OH (US)

(72) Inventors: Nick E. Ciavarella, Seven Hills, OH (US); John P. Cichello, Wooster, OH (US); Jackson W. Wegelin, Stow, OH (US); Aaron D. Marshall, Silver Lake, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 17/882,857

(22) Filed: Aug. 8, 2022

(65) Prior Publication Data

US 2023/0051196 A1 Feb. 16, 2023

Related U.S. Application Data

(60) Provisional application No. 63/232,245, filed on Aug. 12, 2021.

(51) Int. Cl.
*A47K 5/12* (2006.01)
(52) U.S. Cl.
CPC .... *A47K 5/1217* (2013.01); *A47K 2005/1218* (2013.01)
(58) Field of Classification Search
CPC .......... B67D 1/0802; B67D 2001/0824; B67D 2001/0825; B67D 3/0064; A47K 5/1217; A47K 2005/1218; B05B 9/0861
See application file for complete search history.

(56) References Cited

U.S. PATENT DOCUMENTS

| 4,046,289 | A  | * | 9/1977 | Teranishi | A45D 27/10 |
|           |    |   |        |           | 366/147 |
| 9,138,109 | B1 |   | 9/2015 | Leon |  |
| 9,763,546 | B2 |   | 9/2017 | Yang et al. |  |
| 11,337,562 | B2 | * | 5/2022 | Russier | B05B 9/0413 |
| 2004/0050875 | A1 | * | 3/2004 | Kobayashi | G01F 13/005 |
|           |    |   |        |           | 222/383.2 |
| 2007/0000941 | A1 | * | 1/2007 | Hadden | A47K 5/1217 |
|           |    |   |        |           | 222/63 |
| 2009/0026225 | A1 | * | 1/2009 | Lickstein | B05B 9/0861 |
|           |    |   |        |           | 222/325 |

(Continued)

OTHER PUBLICATIONS

International Search Report and Written Opinion from PCT/US2022/039690 dated Nov. 8, 2022.

*Primary Examiner* — Vishal Pancholi
*Assistant Examiner* — Robert K Nichols, II
(74) *Attorney, Agent, or Firm* — Calfee, Halter & Griswold LLP (57) ABSTRACT

Exemplary embodiments of tabletop dispensers are disclosed herein. An exemplary tabletop dispenser for dispensing soap, sanitizer or lotion includes a bottle. The bottle has a neck that has a neck diameter. A pump assembly having a cylindrical housing is also included. The cylindrical has a cylindrical housing diameter that is less than the neck diameter. A controller board, a battery, a motor and a pump are at least partially located within the cylindrical housing. The pump assembly is configured to be located within the neck and the bottle. A sensor for sensing an object and an outlet nozzle are also included.

20 Claims, 6 Drawing Sheets

(56) References Cited

U.S. PATENT DOCUMENTS

2013/0200097 A1* 8/2013 Yang ................ B65D 25/00
                                                        222/52
2018/0263432 A1* 9/2018 Yang ................ B65D 25/00
                                                        222/52
2018/0360276 A1* 12/2018 Yang .............. F04B 43/0063

* cited by examiner

TOUCH-FREE TABLETOP DISPENSERS

TECHNICAL FIELD

The present invention relates generally to touch-free tabletop soap and sanitizer dispensers and more particularly to touch-free tabletop dispensers having pumps, motors and electronics located within the container.

BACKGROUND OF THE INVENTION

In touch-free (or hands-free) dispensers, a liquid or foam pump is activated by a drive actuator throughout a set drive cycle to dispense a selected volume or dose of fluid. The drive actuator is often powered by a battery or other rechargeable power source which is used to drive a direct current motor and a drive train. These legacy touch-free systems are often large and bulky and mounted to a wall or surface. The size of the dispensers may also limit the locations in which the dispenser can be used.

In addition, access to the nozzle is generally restricted to access from the front of the dispenser. Thus, there is a need for a touch-free tabletop dispenser that can operate in a wide variety of locations and that provides access to the nozzle from all directions.

SUMMARY

Exemplary embodiments of tabletop dispensers are disclosed herein. An exemplary tabletop dispenser for dispensing soap, sanitizer or lotion includes a bottle. The bottle has a neck that has a neck diameter. A pump assembly having a cylindrical housing is also included. The cylindrical has a cylindrical housing diameter that is less than the neck diameter. A controller board, a battery, a motor and a pump are at least partially located within the cylindrical housing. The pump assembly is configured to be located within the neck and the bottle. A sensor for sensing an object and an outlet nozzle are also included.

An exemplary touch-free pump assembly for a bottle having a neck is also disclosed herein. The touch-free pump assembly includes a sealed housing configured to fit through the neck of the bottle. The assembly further includes controller board; a motor; a pump; and a battery located within the sealed housing. A pump inlet located proximate a bottom of the sealed housing. The pump assembly further includes a pump outlet, an outlet nozzle and a conduit that connects the pump outlet to the outlet nozzle. Also included is an object sensor and a cap. The pump, the motor and the battery are arranged in a vertical orientation. The cap is configured to secure the sealed housing to the bottle and when the touch-free pump assembly is connected to the bottle, the sealed housing is located within the neck and the bottle.

Another exemplary tabletop sanitizer dispenser includes a bottle having a reservoir for containing sanitizer, a nozzle, a sensor for detecting a hand of a user positioned below the nozzle and a pump assembly. The pump assembly includes a sealed housing extending into the reservoir of the bottle, a power source; a controller board; a motor; and a pump located within the sealed housing; and a pump inlet through the sealed housing. An exemplary touch-free sanitizer dispenser includes a bottle that forms a reservoir for containing sanitizer, a nozzle, a sensor for detecting a hand of a user positioned below the nozzle, and a pump assembly. The pump assembly includes a housing that extends into the reservoir, a pump, and a pump inlet arranged between the pump and a bottom of the reservoir.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

The following description refers to the accompanying drawings, which illustrate specific embodiments of the present disclosure. Other embodiments having different structures and operation do not depart from the scope of the present disclosure.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 5% of still more preferably within 1% of, and most preferably within 0.1% of).

Referring now to FIGS. 1-11, illustrations of an exemplary tabletop dispenser 100 are shown. In this exemplary embodiment, tabletop dispenser 100 is described as being a sanitizer dispenser, however, the dispensers shown and described herein may be a sanitizer dispenser, a soap dispenser, a lotion dispenser, or the like. The dispenser 100 includes a nozzle 102 having a nozzle outlet 104 for dispensing hand sanitizer when a user's hand is detected by a sensor 106.

Hand sanitizer is supplied to the nozzle 102 from a bottle 110 via a pump assembly 120. The pump assembly 120 is attached to the bottle 110 via a cap 108. The cap 108 attaches to a neck 112 of the bottle 110 after the bottle is filled with hand sanitizer. The connection between the cap 108 and the neck 112 can take on a wide variety of forms, such as, for example, a threaded connection, a quarter-turn connection, a snap connection, or other removable and replicable configurations. In addition, permanent or semi-permanent connections, such as, for example, a barbed connection, a press fit connection, an adhesive connection, a welded connection, may be used.

The neck 112 of the bottle 110 has a smaller diameter than the rest of the bottle 110 and includes a mouth or opening 114 that facilitates filling the bottle 110 with hand sanitizer. The bottle 110 encloses a reservoir 116 for holding the hand sanitizer and has a bottom 118. The bottom 118 of the bottle 110 is shaped to provide improved stability when the bottle 110 is placed on a tabletop or other approximately horizontal surface. In the illustrated embodiment, stability is provided to the bottom via an indentation or concavity in the center of the bottom so that the surface area of the bottle that is in contact with the tabletop is arranged towards the outer perimeter of the bottle 110.

After the bottle 110 has been filled with hand sanitizer, the pump assembly 120 is inserted into the bottle 110 through the mouth 114 of the neck 112 and is secured to the neck 112 of the bottle 110 with the cap 108. Where the connection between the cap 108 and the neck 112 is a repeatable connection, the pump assembly 120 can be removed from the bottle 110 to facilitate refilling of the bottle 110 or re-use of the pump assembly 110 with another bottle.

The pump assembly 120 is enclosed by a cylindrical housing 122 that includes a flange 124 that engages the neck 112 of the bottle 110 when the pump assembly 120 is inserted into the mouth 114 of the bottle 110. Cylindrical housing 122 has an outer diameter that is smaller than the inner diameter of mouth 114. The cap 108 secures the flange 124 against the neck 112 of the bottle 110 to form a seal between the pump assembly 120 and the bottle 110 to prohibit leakage of hand sanitizer from the reservoir 116.

The cylindrical housing 122 is open at a top end and extends into the bottle 110 to an opening proximate the bottom end that attaches to a pump 126 and forms a pump inlet 128. Locating the pump inlet 128 at the bottom of the pump assembly 120 allows the dispenser to dispense hand sanitizer from the reservoir 116 until the reservoir 116 is almost or completely empty, lengthening the time that the dispenser 100 can be used before it runs out and is disposed of or is refilled. While the pump 126 is shown as a gear pump (see FIG. 11), other types of pumps can be used to move fluid from the reservoir 116 to the nozzle outlet 104, such as, for example, displacement pumps, diaphragm pumps or the like.

Figure 1:
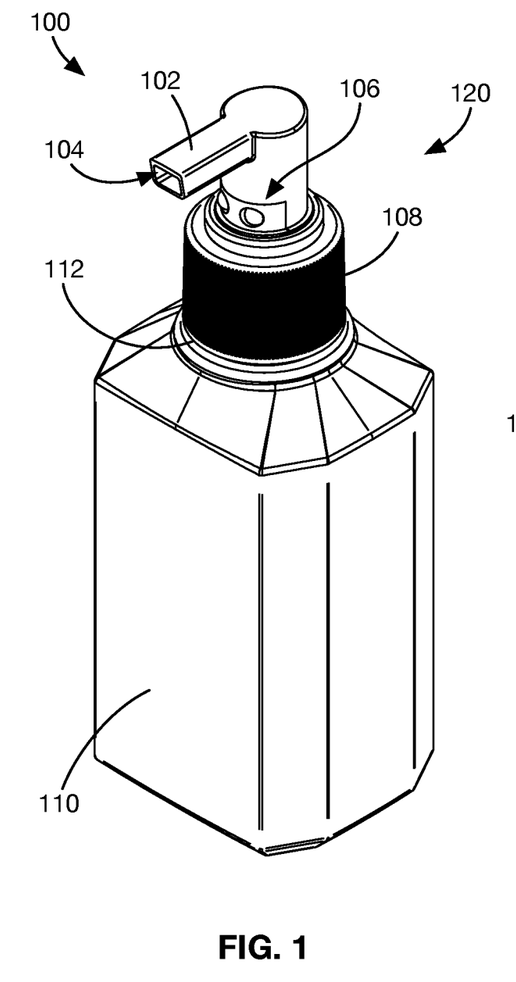
FIG. 1 is a perspective view of an exemplary soap or sanitizer dispenser.
Figure 2:
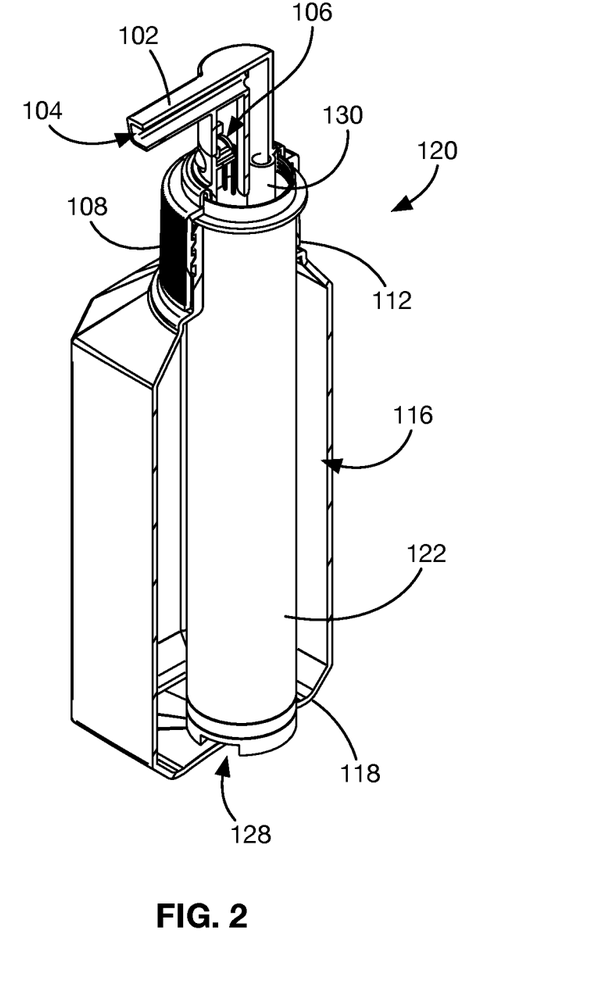
FIG. 2 is a perspective partial cross-sectional view of the exemplary soap or sanitizer dispenser of FIG. 1.
Figure 3:
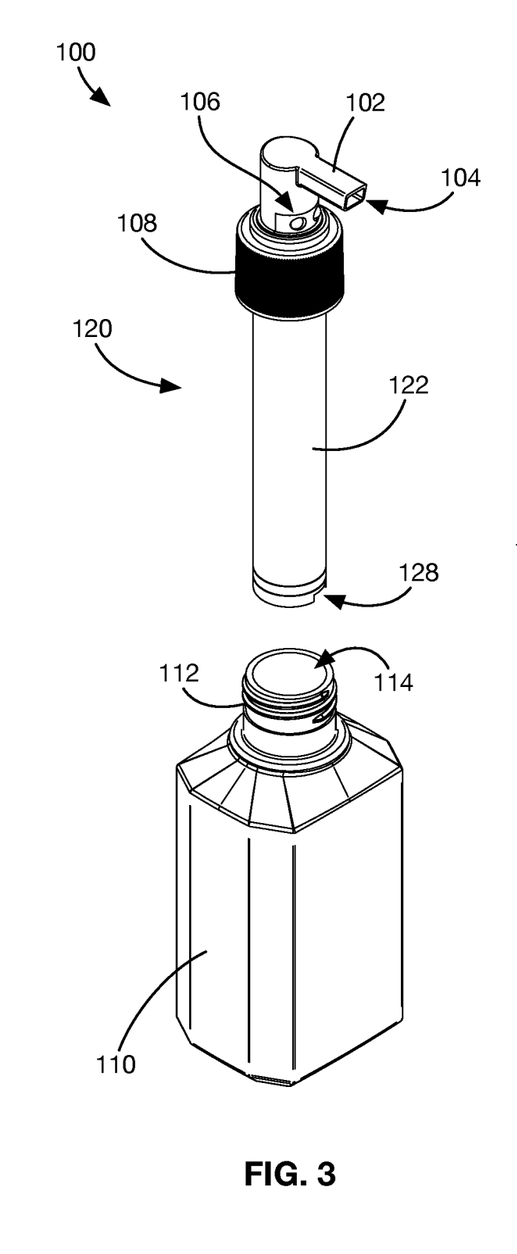
FIG. 3 is an exploded view of the exemplary soap or sanitizer dispenser of FIG. 1.
Figure 4:
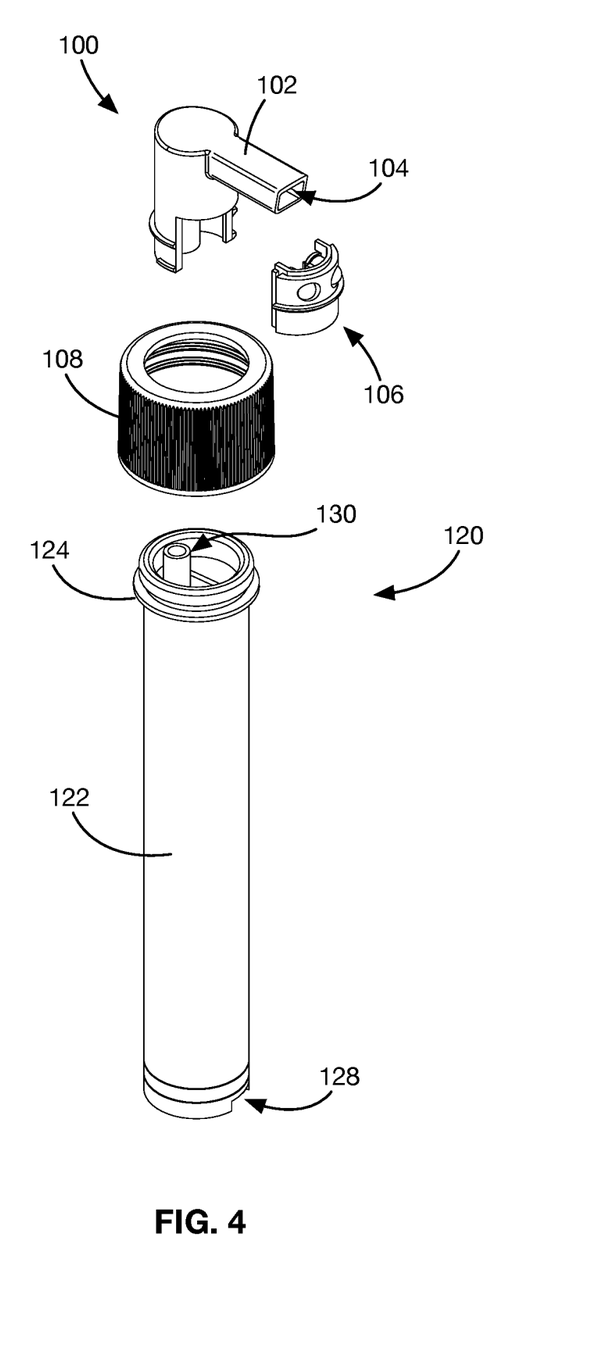
FIG. 4 is an exploded view of a pump assembly of the exemplary soap or sanitizer dispenser of FIG. 1.
Figure 5:
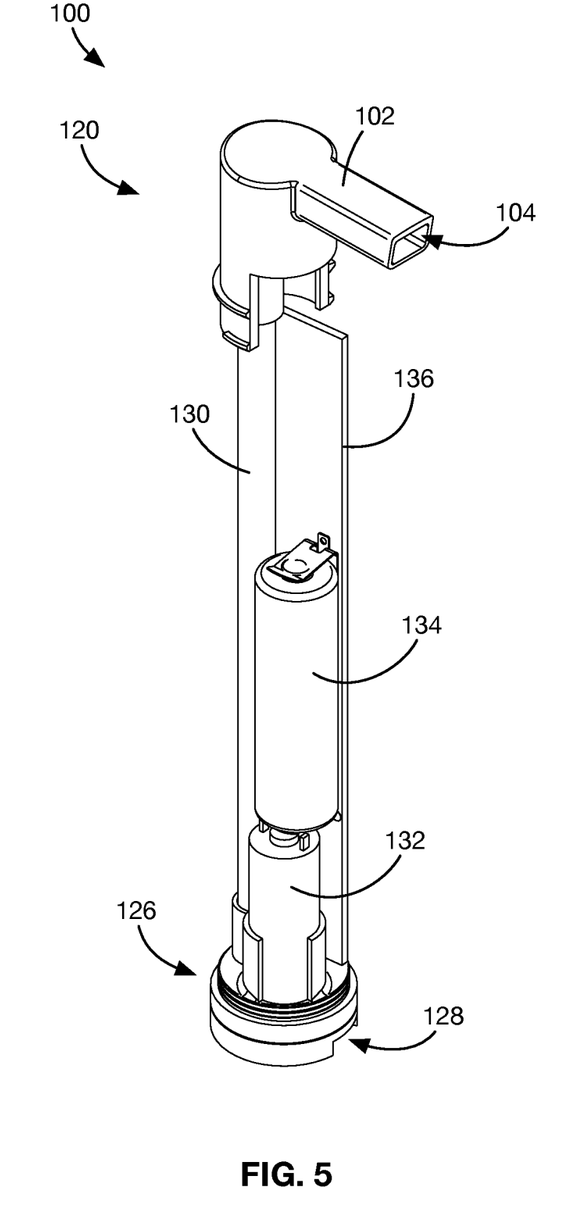
FIG. 5 is a perspective view of the pump assembly of FIG. 4 with the pump housing removed.
Figure 6:
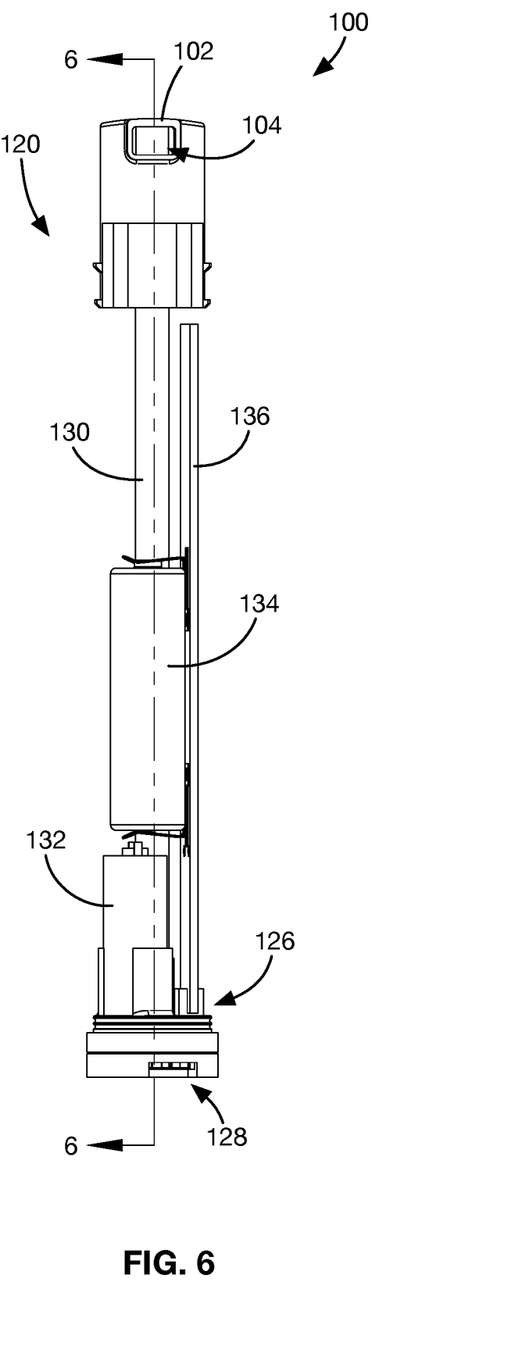
FIG. 6 is a front view of the pump assembly of FIG. 5.
Figure 7:
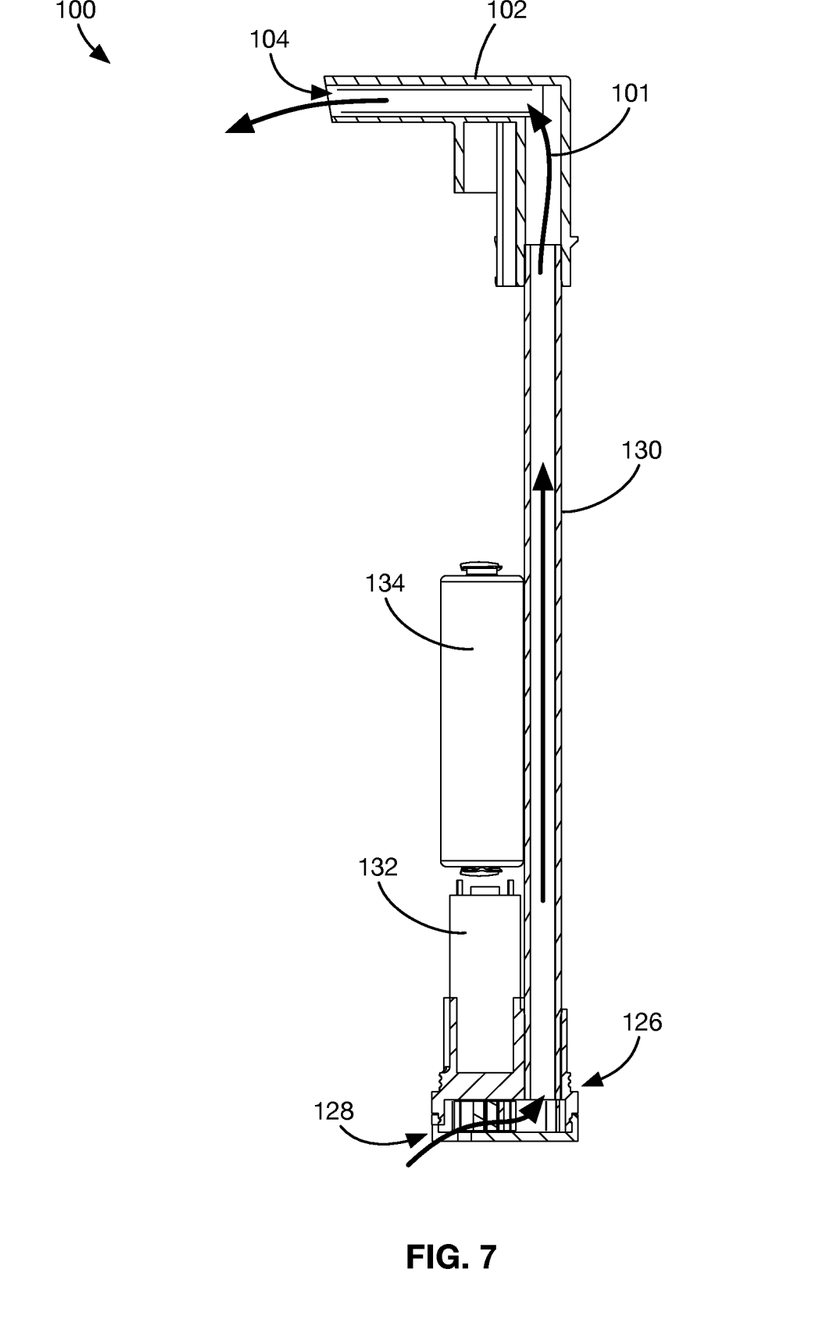
FIG. 7 is a cross-sectional view of the pump assembly of FIG. 5 taken along the line 6-6 of FIG. 6.

Referring now to FIGS. 5-7, the pump assembly 120 is shown assembled to the nozzle 102 and with the cylindrical housing 122 removed to expose the components of the pump assembly 120. The pump assembly 120 includes the pump 126, an outlet tube 130, a motor 132, a battery 134, and a controller board 136. The motor 132 is attached to the pump 126 and, when operated, causes the pump 126 to pump hand sanitizer from the reservoir 116 via the pump inlet 128. The operation of the pump 126 and the path of the hand sanitizer through the pump assembly 120 from the pump inlet 128 to the nozzle outlet 104 is described in greater detail below. The battery 134 provides electrical power to the electrical components of the dispenser 100—i.e., the motor 132, the controller board 136, and the sensor 106. The battery 134 can be a removable battery that can be changed during maintenance of the dispenser 100 or can be an integrated battery that is permanently attached to the controller board 136.

Battery 134 may be a AA battery or a AAA battery, and accordingly, battery 134 may have an operating voltage of about 1.5 volts. If two AA batteries or two AAA batteries are used, the operating voltage may be about 3 volts. Thus, in some embodiments, the motor 132 must be selected to operate at about 1.5 volts. In some embodiments, motor 132 must be selected to operate at about 3 volts. In some embodiments, controller board 136 includes boost circuitry (not shown) to increase the voltage delivered to the motor 132.

In this exemplary embodiment, motor 132 has an operating range of about 0.9 to about 1.6 volts.

The flow of the hand sanitizer fluid from the reservoir 116 to the nozzle outlet 104 is indicated by flow path arrows 101 as shown in the cross-sectional view of the pump assembly 120 in FIG. 7. When the pump 126 is operated, hand sanitizer is drawn into the pump 126 from the reservoir 116 through the pump inlet 128. The hand sanitizer fluid is pumped through the pump 126 to the outlet tube 130. The outlet tube 130 extends from the pump 126 to the nozzle 102 to fluidly connect the pump 126 to the nozzle outlet 104. The hand sanitizer is pumped through the outlet tube 130 by the pump 126 until the hand sanitizer fluid is dispensed from the nozzle outlet 104 onto the user's hand.

The pump 126 and the connection between the pump 126 and the motor 132 are shown in FIGS. 8-11. The pump 126 includes a top cover 138 and a bottom cover 140. The top cover 138 includes a mating portion 142—such as a threaded or press-fit portion—that attaches the top cover 138 to the pump housing 122 and a motor mount 144 for receiving the motor 132. The bottom cover 140 is attached to the top cover by any suitable means, such as, for example, a threaded connection, an adhesive connection, a press fit connection, or the like. The top cover 138 and the bottom cover 140 enclose a drive gear 146 and a driven gear 148 (FIG. 11) that are rotated by operation of the motor 132 to cause the pump 126 to pump hand sanitizer fluid through the pump inlet 128 that is provided in the bottom cover 140.

Figure 8:
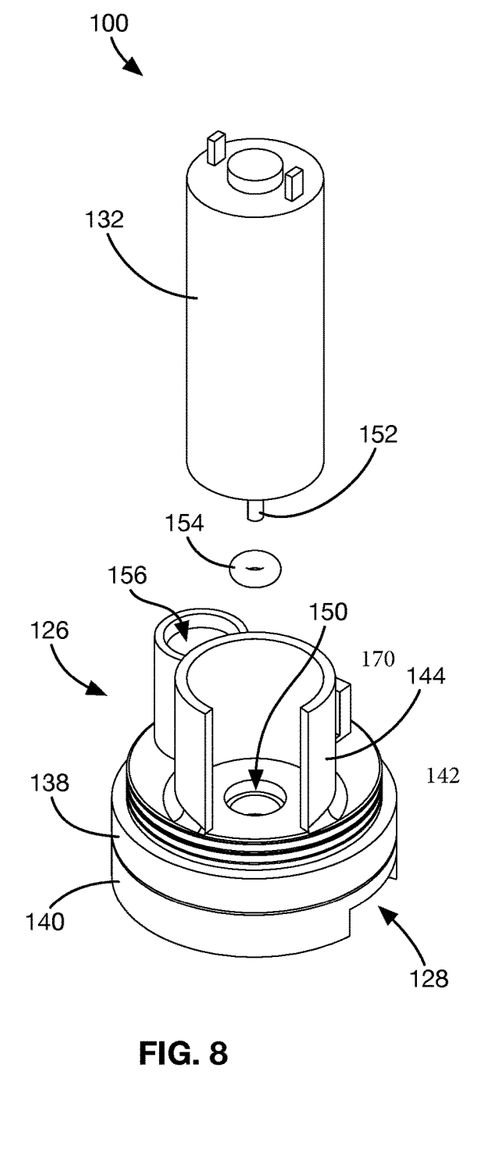
FIG. 8 shows a top perspective exploded view of the pump and the pump motor.
Figure 9:
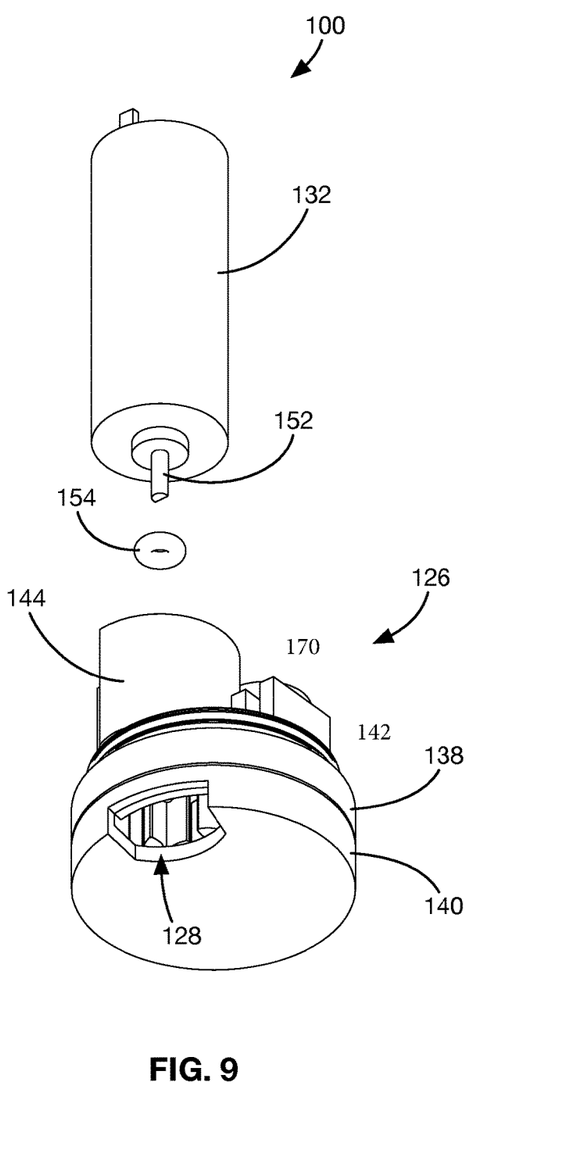
FIG. 9 shows a bottom perspective exploded view of the pump and the pump motor.
Figure 10:
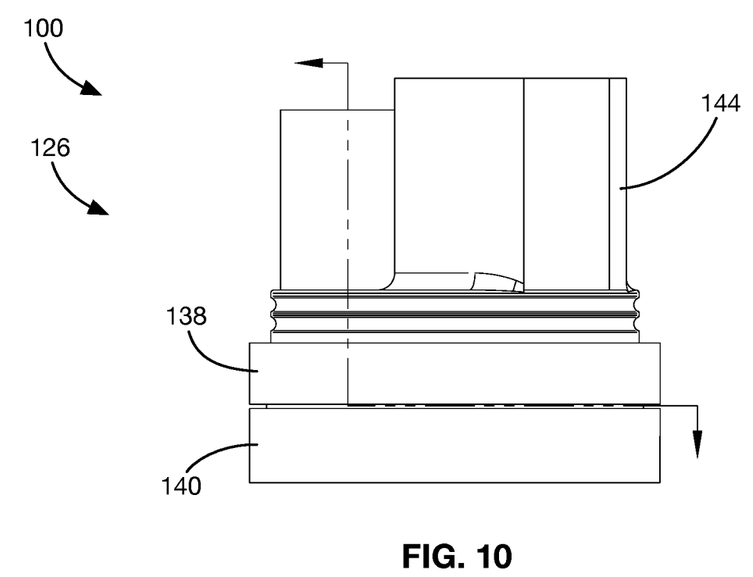
FIG. 10 shows a side view of the pump.
Figure 11:
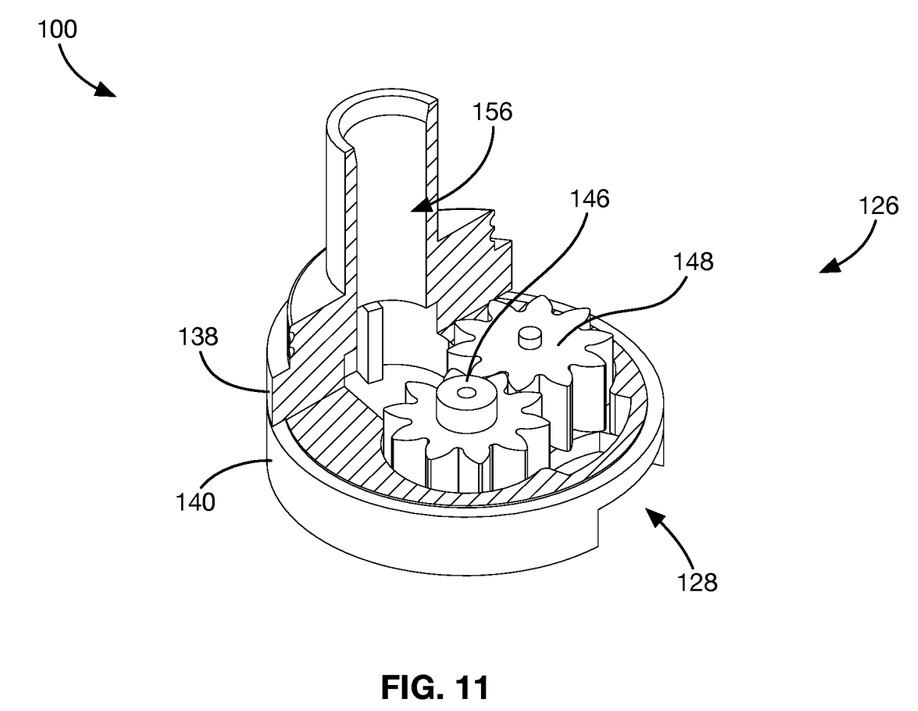
FIG. 11 shows a perspective cross-sectional view of the pump of FIG. 10 taken along the line 10-10 of FIG. 10.

As can be seen in FIG. 8, the top cover 138 includes a shaft opening 150 through the top cover 138 at the bottom of the motor mount 144 to allow a shaft 152 of the motor 132 to pass through the top cover 138 to engage the drive gear 146. The drive gear 146 and driven gear 148 are enmeshed such that rotation of the drive gear 146 causes the driven gear 148 to rotate. (See FIG. 11.) A shaft seal 154 fits within or against the shaft opening 150 to form a seal between the shaft 152 of the motor 132 and the top cover 138 to prohibit leakage from the pump 126 into the pump assembly 120. The shaft seal 154 can take on a wide variety of forms and is any suitable seal for use as a dynamic seal around the shaft of a motor, such as, for example, an O-ring, a bushing, a pressure-assisted seal, a wiper seal, or the like.

In addition, top cover 138 includes a holder 170 for receiving an end of controller board 136 to retain controller board 136. In some embodiments, battery 134 is secured to controller board 136. In some embodiments, motor 132 is secured to controller board 136. Accordingly, when motor 132 is inserted into motor mount 144 and the end of controller board 136 is inserted into holder 170, the controller board 136, motor 132 and battery 134 are held securely within cylindrical housing 122.

Battery 134, motor 132 and pump 128 are arranged in a vertical orientation, i.e. they are arranged one above the other. In this exemplary embodiment, the battery 132 is located above the motor 132, which is located above the pump 128. In some embodiments, the battery 134 is below the motor 132 and the pump 128.

During operation of the dispenser 100, the sensor 106 detects the presence of one or more of the user's hands placed below the nozzle 102. The sensor 106 can be any suitable sensor for detecting the presence of a hand or hands below the nozzle 102 and just in front of the sensor 106, such as, for example, an infrared sensor, a proximity sensor, a camera, a capacitance sensor, or the like. The sensor 106 sends a signal to the controller board 136 indicating that the user's hand has been detected. Controller board 136 includes a processor (not shown) and memory (not shown). upon detection of a hand, the controller board 136 then causes the motor 132 to rotate the shaft 152 that is attached to the drive gear 146 of the pump 126. Rotation of the drive gear 146 causes the driven gear 148 to rotate in turn, thereby moving fluid inside the pump 126 from the pump inlet 128 to a pump outlet 156. As the drive gear 146 and driven gear 148 continue to be rotated by the motor 132, the hand sanitizer is pumped through the pump 126 to move the fluid through the pump outlet 156, through the outlet tube 130, through the nozzle 102, and out of the nozzle outlet 104 into the hands of the user. The controller board 136 can control the pump 126 to run for a predetermined duration or until a predetermine amount of fluid has been dispensed.

In some embodiments, an on/off switch (not shown) is located on top of nozzle 102. An on/off switch allows dispenser 100 to be moved to different locations without dispensing fluid when dispenser 100 is being moved.

In some embodiments, sensor 106 has a small sensing range so that sensor 106 will only detect a hand that is in very close proximity to the nozzle outlet 104. In some embodiments, the range of sensor 106 is limited to about 102 millimeters ("mm"). In some embodiments, the range of sensor 106 is limited to about 90 mm. In some embodiments, the range of sensor 106 is limited to about 85 mm. In some embodiments, the range of sensor 106 is limited to about 80 mm. In some embodiments, the range of sensor 106 is limited to about 75 mm. In some embodiments, the range of sensor 106 is limited to about 70 mm. In some embodiments, the range of sensor 106 is limited to about 65 mm. In some embodiments, the range of sensor 106 is limited to about 60 mm. In some embodiments, the range of sensor 106 is limited to about 56 mm. In some embodiments, the range of sensor 106 is limited to about 52 mm. In some embodiments, the range of sensor 106 is limited to about 50 mm. In some embodiments, the range of sensor 106 is limited to about 45 mm. In some embodiments, the range of sensor 106 is limited to about 40 mm. In some embodiments, the range of sensor 106 is limited to about 35 mm. In some embodiments, the range of sensor 106 is limited to about 30 mm. In some embodiments, the range of sensor 106 is limited to about 25 mm. In some embodiments, the range of sensor 106 is limited to about 20 mm. In some embodiments, the range of sensor 106 is limited to about 15 mm. Limiting the range of sensor 106 allows the dispenser 100 to be picked up and moved without false triggering of the sensor 106.

The cylindrical housing 122 is located entirely within the bottle 110 and the bottle neck 112. In some embodiments, the bottle neck 112 has an inside diameter of 1 inch. Accordingly, in some embodiments, the cylindrical housing has an outside diameter that is less than 1 inch. In some embodiments, the bottle neck 112 has an inside diameter of 0.9 inches. Accordingly, in some embodiments, the cylindrical housing has an outside diameter that is less than 0.9 inches. In some embodiments, the bottle neck 112 has an inside diameter of 0.08 inches. Accordingly, in some embodiments, the cylindrical housing has an outside diameter that is less than 0.8 inches. In some embodiments, the bottle neck 112 has an inside diameter of 0.7 inches. Accordingly, in some embodiments, the cylindrical housing has an outside diameter that is less than 0.7 inches.

Pump assembly 120 is inserted into bottle 110 through the neck 114, which has a number of advantages. The integrity of the bottle 110 is maintained and reduces the risk of leak. If the pump assembly 120 is inserted from the bottom of the bottle, or container, the bottle or container needs to be connected together and may leak. In addition, when the cylindrical housing 122 is removed from the bottle 110, residual fluid in the bottle 110 remains in the bottle and does not spill out. If the bottom of the bottle or container is removed when residual fluid is in the container, the residual fluid would spill out.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A tabletop dispenser for dispensing soap, sanitizer or lotion comprising:
a bottle:
the bottle forming a reservoir;
the bottle having a neck;
the neck having a neck diameter that is smaller than a diameter of the bottle; wherein the neck has a top and a bottom; wherein the bottom of the neck opens into the reservoir;
a pump assembly having
a cylindrical housing;
the cylindrical housing having a cylindrical housing diameter;
the cylindrical housing diameter is less than the neck diameter;
a controller board;
a battery;
a motor; and
a pump;
wherein the controller board, battery and motor are located within the cylindrical housing; wherein the controller board, motor and battery are located below the top of the neck of the bottle and wherein one or more of the controller board, motor and battery are located below the bottom of the neck; and
wherein the cylindrical housing is located within the neck and the bottle;
a sensor for sensing an object; and
an outlet nozzle; and
wherein when the reservoir is filled with a fluid, the fluid surrounds at least a portion of the cylindrical housing.

2. The tabletop dispenser of claim 1 wherein the battery, motor and pump are arranged in a vertical arrangement.

3. The tabletop dispenser of claim 2 wherein the battery is located above the motor and the pump.

4. The tabletop dispenser of claim 1 wherein the battery comprises a single 1.5 volt battery.

5. The tabletop dispenser of claim 1 wherein the sensor for sensing an object and the outlet nozzle and are connected to the pump assembly and removed with the pump assembly.

6. The tabletop dispenser of claim 1 wherein the pump assembly is inserted and removed through the neck of the bottle.

7. The tabletop dispenser of claim 1 wherein the bottle is devoid of any openings other than the opening in the neck of the bottle.

8. The tabletop dispenser of claim 1 wherein the sensor is an infrared sensor.

9. The tabletop dispenser of claim 1 wherein the sensor has a sensing range of less than 52 millimeters.

10. A touch-free pump assembly for a bottle having a neck, wherein the interior of the bottle forms a reservoir, comprising:
a sealed housing configured to fit through the neck of the bottle;
wherein the neck of the bottle has a smaller diameter then a lower portion of the bottle;
wherein at least a portion of the sealed housing is located within the reservoir of the bottle;
wherein the neck has a top and a bottom;
wherein the bottom of the neck opens into the reservoir;
a controller board; a motor; and a battery located within the sealed housing;
wherein the controller board, motor and battery are located below the top of the neck of the bottle and wherein one or more of the controller board, motor and battery are located below the bottom of the neck;
a pump;
a pump inlet located proximate a bottom of the sealed housing;
a pump outlet;
an outlet nozzle;
a conduit connecting the pump outlet to the outlet nozzle;
an object sensor; and
a cap;
wherein the pump, the motor and the battery are arranged in a vertical orientation;
wherein the cap is configured to secure the sealed housing to the bottle;
wherein when the touch-free pump assembly is connected to the bottle, the sealed housing is located within the neck and the bottle; and
wherein when the reservoir of the bottle is filled with fluid, the fluid at least partially surrounds the sealed housing.

11. The pump assembly of claim 10 wherein the battery is located above the motor.

12. The pump assembly of claim 10 wherein the pump is located at least partially within the sealed housing.

13. The pump assembly of claim 10 wherein the pump comprises two or more gears.

14. The pump assembly of claim 10 wherein the battery is a 1.5 volt battery.

15. The pump assembly of claim 10 wherein the object sensor has a sensing range of less than about 60 millimeters.

16. A tabletop sanitizer dispenser comprising:
a bottle comprising a reservoir for containing sanitizer;
the bottle having a neck;
the neck having a smaller diameter than a diameter of the bottle;
a nozzle;
a sensor for detecting a hand of a user positioned below the nozzle;
a pump assembly comprising:
a sealed housing extending through the neck of the bottle;
wherein the neck has a top and a bottom, and wherein the bottom of the neck opens into the reservoir;
a power source; a controller board; and a motor; located within the sealed housing;
wherein the controller board, motor and battery are located below the top of the neck of the bottle and wherein one or more of the controller board, motor and battery are located below the bottom of the neck;
a pump; and
a pump inlet located proximate the bottom of sealed housing and
wherein when the reservoir of the bottle is filled with fluid, the fluid at least partially surrounds the sealed housing.

17. The tabletop sanitizer dispenser of claim 16, wherein the pump assembly is installed in the bottle by insertion through a neck of the bottle.

18. The tabletop sanitizer dispenser of claim 16, wherein the pump assembly has a width that is less than an inner diameter of a neck of the bottle.

19. The tabletop sanitizer dispenser of claim 16, wherein the pump assembly is only attached to the neck of the bottle.

20. The tabletop sanitizer dispenser of claim 16, wherein the sealed housing is cylindrical.

* * * * *